United States Patent [19]
Anderson

[11] Patent Number: 5,766,126
[45] Date of Patent: Jun. 16, 1998

[54] GONIOMETRIC ROBOTIC ARRANGEMENT

[75] Inventor: Peter Anderson, Bucks, England

[73] Assignee: Armstrong Healthcare Limited, High Wycombe, United Kingdom

[21] Appl. No.: 708,263

[22] Filed: Sep. 6, 1996

[30] Foreign Application Priority Data

Sep. 8, 1995 [GB] United Kingdom .................. 9518402

[51] Int. Cl.$^6$ .......................................................... A61B 1/00
[52] U.S. Cl. .............................................. 600/102; 600/228
[58] Field of Search ................................. 600/102, 227, 600/228, 229, 230; 395/80, 97, 911, 912, 924; 901/27, 28, 29, 30, 50

[56] References Cited

U.S. PATENT DOCUMENTS

| | | | |
|---|---|---|---|
| 5,184,601 | 2/1993 | Putman | 600/102 |
| 5,228,429 | 7/1993 | Hatano | 600/102 |
| 5,372,147 | 12/1994 | Lathrop, Jr. et al. | 600/230 X |
| 5,540,649 | 7/1996 | Bonnell et al. | 600/102 X |
| 5,571,072 | 11/1996 | Kronner | 600/228 X |

Primary Examiner—Beverly M. Flanagan
Attorney, Agent, or Firm—Fulwider Patton Lee & Utecht, LLP

[57] ABSTRACT

In a robotic arrangement an elongate telescope(10) is provided adapted to be inserted into a patient(6). A drive arm(8) is connected to the telescope and means(7) are provided to rotate the drive arm about a substantially vertical axis. Drive means are provided associated with the drive arm(8) to adjust the angle of inclination of the cannula. This may comprise means to adjust the angle of inclination of the drive arm(8) itself.

19 Claims, 6 Drawing Sheets

5,766,126

GONIOMETRIC ROBOTIC ARRANGEMENT

BACKGROUND OF THE INVENTION

THE PRESENT INVENTION relates to a goniometric robotic arrangement and more particularly relates to a goniometric robotic arrangement intended for use in a medical environment.

In a preferred form, the goniometric medical robot of the invention utilises a laparoscope to provide a visual image of part of the interior of a patient. However, it is to be appreciated, that the invention may find other uses.

According to this invention there is provided a goniometric robotic arrangement, the arrangement comprising an elongate telescope adapted to be inserted into the abdomen of a patient, a drive arm connected to means adapted to rotate the drive arm about a substantially vertical axis, connecting means connecting the drive arm to the telescope, and drive means associated with the drive arm to adjust the angle of inclination of the telescope.

In one embodiment the drive arm has an initial inclined position, the lower end of the drive arm being connected by a loose articulation, which comprises a connecting means, to part of said telescope, the upper end of the drive arm being connected to said means which rotate the drive arm, said drive means being adapted to adjust the angle of inclination of the drive arm to effect the adjustment of the angle of inclination of the telescope.

Advantageously the means adapted to adjust the angle of inclination of the drive arm comprise a crown wheel-and-pinion device, which may be driven by a low torque motor. In an alternative embodiment of the invention a carriage is provided which is movable along the drive arm, the carriage comprising said connecting means and being connected to the telescope, said drive means being adapted to move the carriage along the drive arm to effect the adjustment of the angle of inclination of the telescope.

Preferably the support arm is horizontal.

Preferably the means adapted to rotate the drive arm are supported by support means, further drive means being provided to drive the support means in a vertical direction.

Conveniently the support means comprises a substantially horizontally extending support beam, supported by an elongate substantially vertical support member, the said drive means being adapted to drive the support member.

Advantageously the support member is received within a housing, the housing being mounted on casters or the like. The means to drive the support means vertically may comprise a hydraulic mechanism or a recirculating ball drive, which may be driven by a low torque motor.

Preferably the means adapted to rotate the drive arm comprise a motor contained within a motor housing, a substantially vertical drive shaft driven by the motor being connected to one end of the drive arm.

Conveniently the telescope is associated with a camera provided at the upper end of the telescope. The lower end of the telescope may be optically cranked. Means may be provided to rotate at least the lower end of the telescope relative to the axis of the telescope.

Conveniently the arrangement is provided with two light sources generating intersecting beams of light, the arrangement being such that the intersecting beams of light are adjusted to intersect at a position a predetermined distance beneath the upper end of the drive arm.

In order that the invention may be more readily understood, and so that further features thereof may be appreciated, the invention will now be described, by way of example, with reference to the accompanying drawings.

DETAILED DESCRIPTION OF THE PREFERRED EMBODIMENTS

Figure 1:
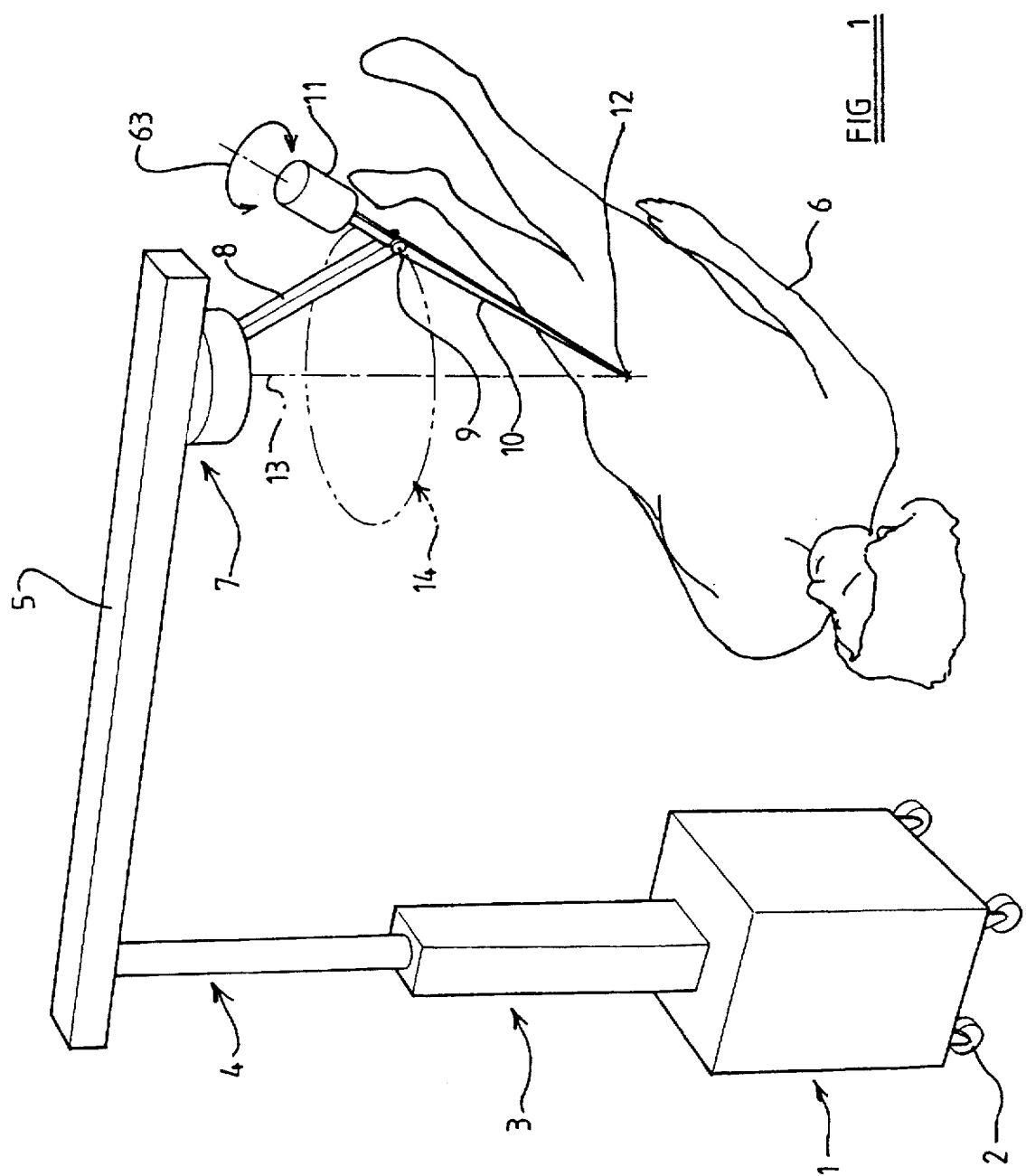
FIG. 1 is a perspective view of one embodiment of the invention.

Referring initially to FIG. 1, a goniometric robotic apparatus in accordance with the invention comprises a housing 1, which may be mounted on rollers or casters 2 for ease of movement. A vertical support column 3 extends upwardly from the housing and telescopically receives an elongate vertical support member 4. The elongate support member 4 may be driven upwardly and downwardly by an appropriate mechanism. The mechanism may comprise a hydraulic mechanism, but preferably comprises a low torque electric motor associated with a direct drive mechanism such as a re-circulating ball drive.

The elongate support member 4 supports, at its upper end, a horizontally extending support beam 5. The horizontal support beam 5 extends laterally beyond the housing 1 so that a terminal portion of the support beam can be located above a patient 6. The beam 5 carries, at a position located directly above the patient, a motor housing 7. A drive arm 8 extends from beneath the motor housing 7, the free end of the drive arm 8 being connected by a loose articulation 9 to a central part of a telescope 10, comprising part of a laparoscope. The drive arm 8, as will be described in greater detail below, has one end on the vertical axis of the rotation of a drive shaft of a motor, and the other end offset, both horizontally and vertically, so the drive arm 8 is inclined to the vertical and to the horizontal. The telescope 10 is associated with a camera 11 provided at the upper end of the telescope.

The lower end of the telescope 10 is inserted through an appropriate incision 12 into the abdomen of the patient 6. The incision 12, which forms the entry point into the patient, lies on a notional extension of the vertical axis of the drive shaft of the motor. The telescope may pass through a short cannula in the region of the incision 12, the cannula forming a gas-tight seal between the telescope and the patient.

Typically the abdomen of the patient will be insufflated with a gas such as nitrogen or carbon dioxide, thus separating the individual organs within the abdomen of the patient. This permits some movement of the end of the telescope within the abdomen of the patient. The gas-tight seal provided at the incision by the cannula prevents unintentional deflation of the patient.

The motor housing 7 contains motors, one of which is adapted to rotate the drive arm 8 about a vertical axis 13, this being the axis of the drive shaft driving the drive arm 8 at its upper end. The axis 13 is coincident with the incision 12. The loose connection 9 thus effects a circular motion as indicated by the dotted line 14, about the axis 13. The telescope thus describes the exterior of a conical surface. The point where the telescope 10 passes through the incision into the abdomen of the patient effectively comprises a goniometric point. Since the connection 9 is a loose connection, as the drive arm 8 is rotated, the telescope 10 associated with the camera 11 is rotated in such a way that no stress is placed on the entry point to the patient.

It is to be appreciated that by rotating the drive arm 8 about the vertical axis 13 in the manner described, the lower end of the telescope, within the abdomen of the patient will execute a "pan" action.

Figure 2:
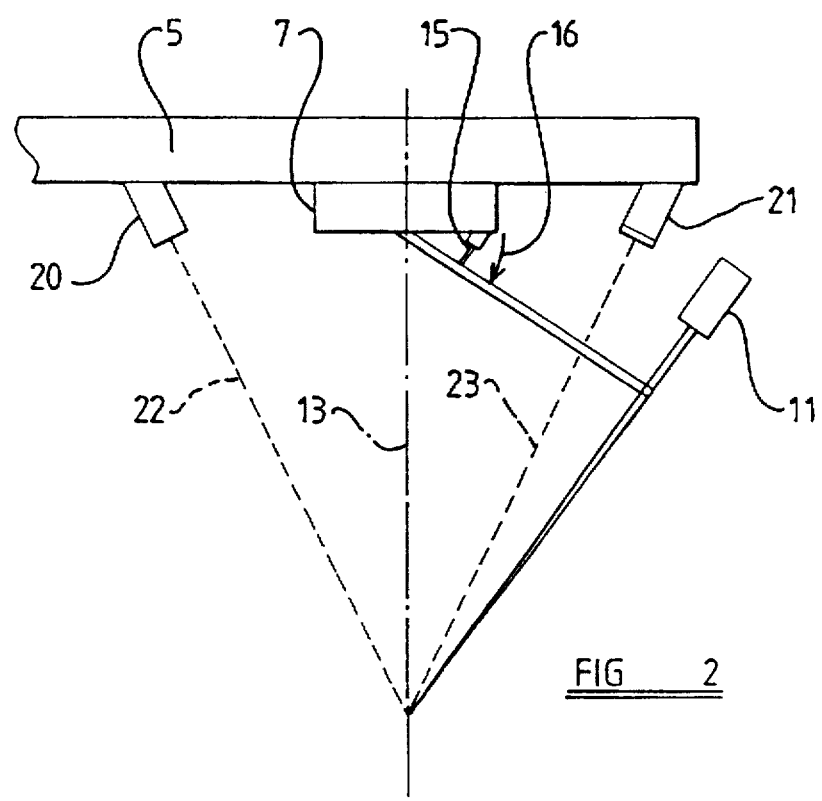
FIG. 2 is a side view of part of the embodiment of FIG. 1.

As can be seen more clearly from FIG. 2, the motor housing 7 is provided with an arrangement, schematically illustrated at 15 which can alter the angle α between the drive arm 8 and the lower surface of the motor housing 7. The arrangement 15 may comprise a crown wheel-and-pinion-type arrangement, with a motor driving the pinion, and the crown wheel being connected to the drive arm 8.

Consequently, it is possible for the angle of inclination β of the drive arm 8 to be adjusted. The drive arm 8 is inclined relative to the vertical axis 13 and relative to the horizontal axis. The degree of inclination may be adjusted by the motor driving the pinion of the crown wheel-and-pinion arrangement.

If the elongate support member 4 is moved upwardly, thus moving the horizontal support beam 5 upwardly, and if the angle α is increased at an appropriate rate, the telescope 10 will occupy the same angle of inclination β, but the lower part of the telescope 10 will be inserted more deeply into the abdomen of the patient. Consequently a "zoom" effect is achieved. The loose coupling 9, and the alignment of the entry point or incision 12 on the axis of rotation of the drive arm 8 ensures that the movement is goniometric movement.

It is also to be appreciated that if the elongate support member 4 is moved upwardly, thus lifting the horizontal support beam 5, and if the angle α between the drive arm 8 and the under-surface of the motor housing 7 is increased at a relatively fast rate, the telescope 10 may be tilted to have a more vertical orientation. Conversely, by a lowering of the support beam 5 and decreasing the angle α, the telescope 10 may be tilted to have a less vertical orientation. Thus a "tilt" function can be achieved. Again, because of the loose connection 9 and the alignment of the incision 12 with the axis of rotation of the drive arm 8 the movement is a goniometric movement.

With appropriate control a "zoom" and a "tilt" may be effected simultaneously. Both of these movements, when effected simultaneously, will be goniometric.

It is to be appreciated that the pan, zoom and tilt function will be achieved by appropriate controls operated by a surgeon or other operative. Appropriate software within a control arrangement will synchronise the upward movement of the elongate element 4 and any change of the angle α to achieve the required zoom or tilt effect. The three motors referred to above, namely the motor that drives the support member 4, the motor which rotates the drive arm 8, and the motor that drives the crown wheel of the crown wheel-and-pinion arrangement 15 are all low torque motors, preferably being direct drive motors with a sufficiently low gearing to permit back driving. If it is desired, for example in an emergency, to move the telescope 10 by hand, this can be done in an easy manner. Alternatively, fluid clutches, or some other form of "slippery" clutch could be incorporated in the drive mechanism to provide the same effect.

As can be seen from FIG. 2, the horizontal support beam 5 is provided with two spaced apart lights 20,21, the lights emitting sharply defined light beams 22,23 which are inclined inwardly towards one another. The beams intersect at a point on the axis 13. The arrangement is such that when the beam 5 is a predetermined distance above the abdomen of a patient, a position which may be termed an "initialising" position, the two light beams intersect each other on the skin of the patient. It is thus possible to move the horizontal support beam to a predetermined position relative to the skin of the patient, the two light beams each illuminating the part of the skin of the patient that will be where the incision 12 is located. This initial "initialising" of the apparatus is linked to controlling software to cause appropriate combinations of vertical motions of support member 4 and inclination of drive arm 8, to produce zoom or tilt motion of the telescope. These motions will be goniometric.

Figure 3:
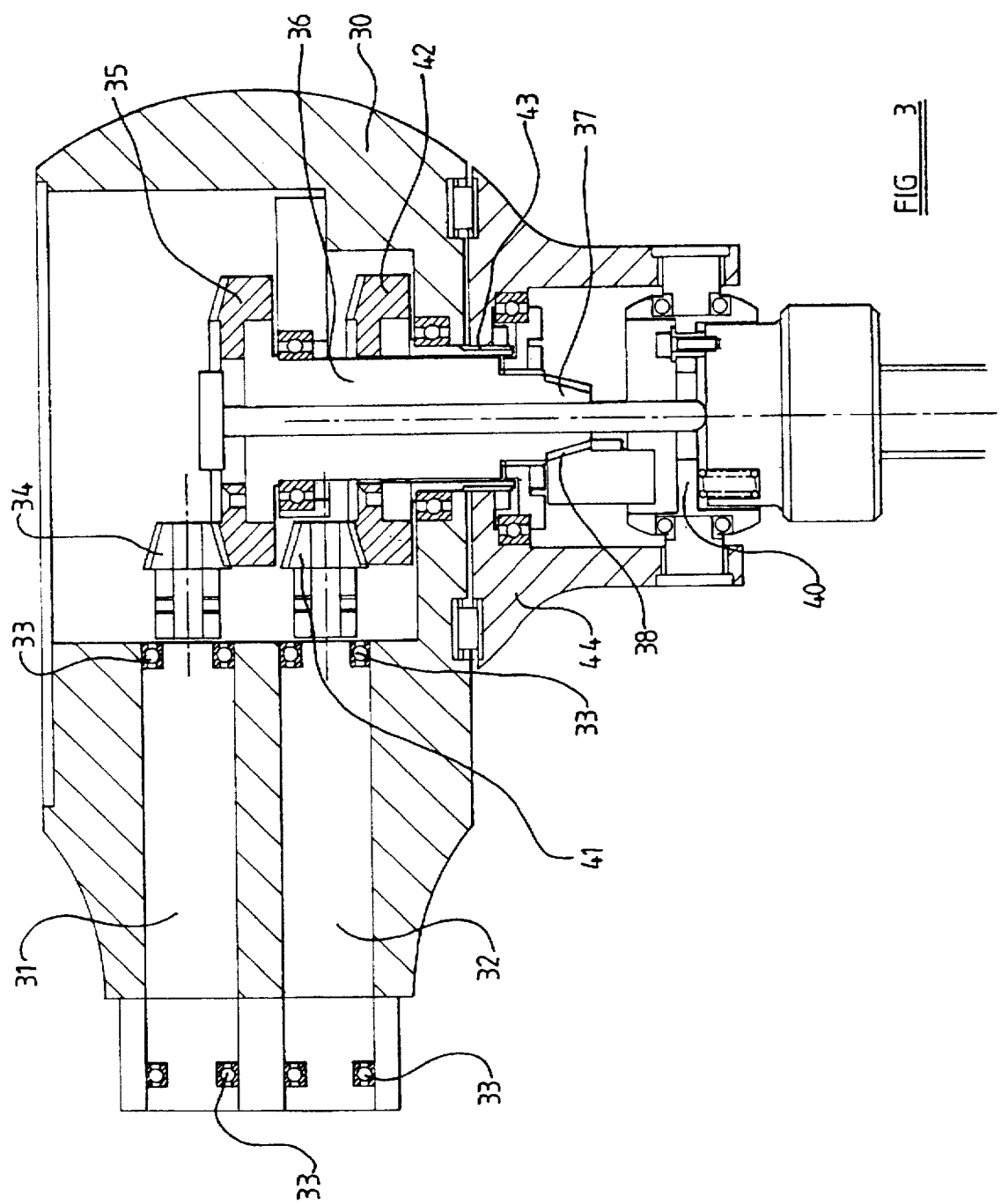
FIG. 3 is a diagrammatic sectional view of part of an alternative embodiment.
Figure 5:
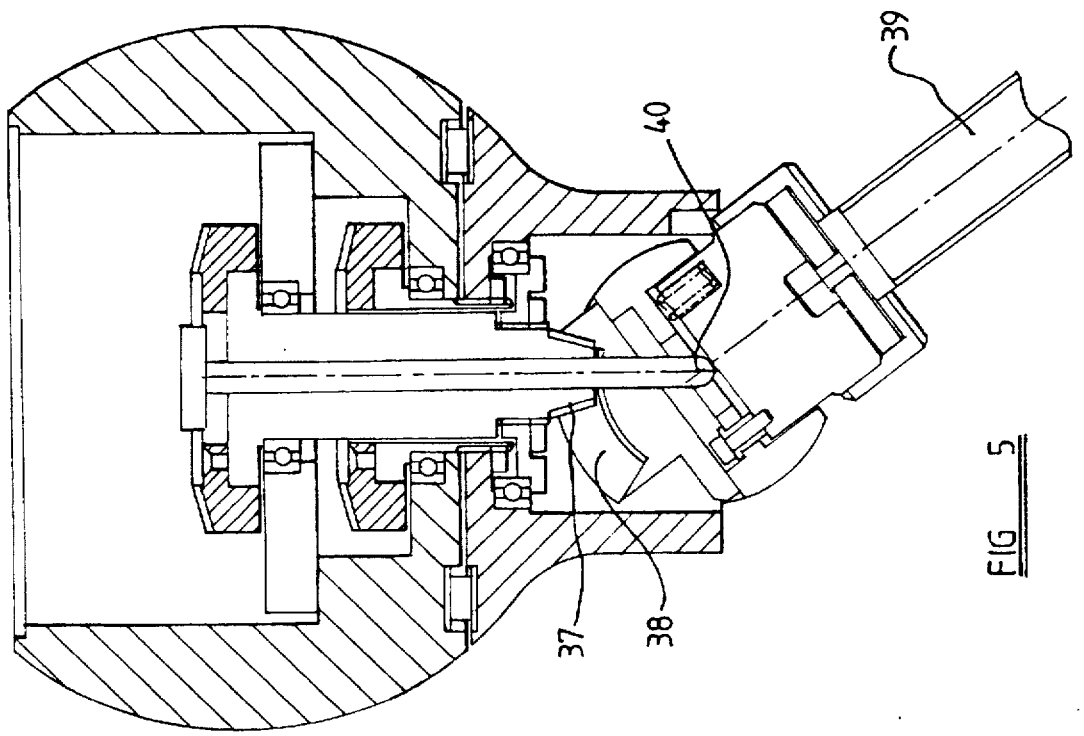
FIG. 5 is a further sectional view corresponding to FIG. 4 showing the apparatus of FIG. 3 in an alternate position.
Figure 4:
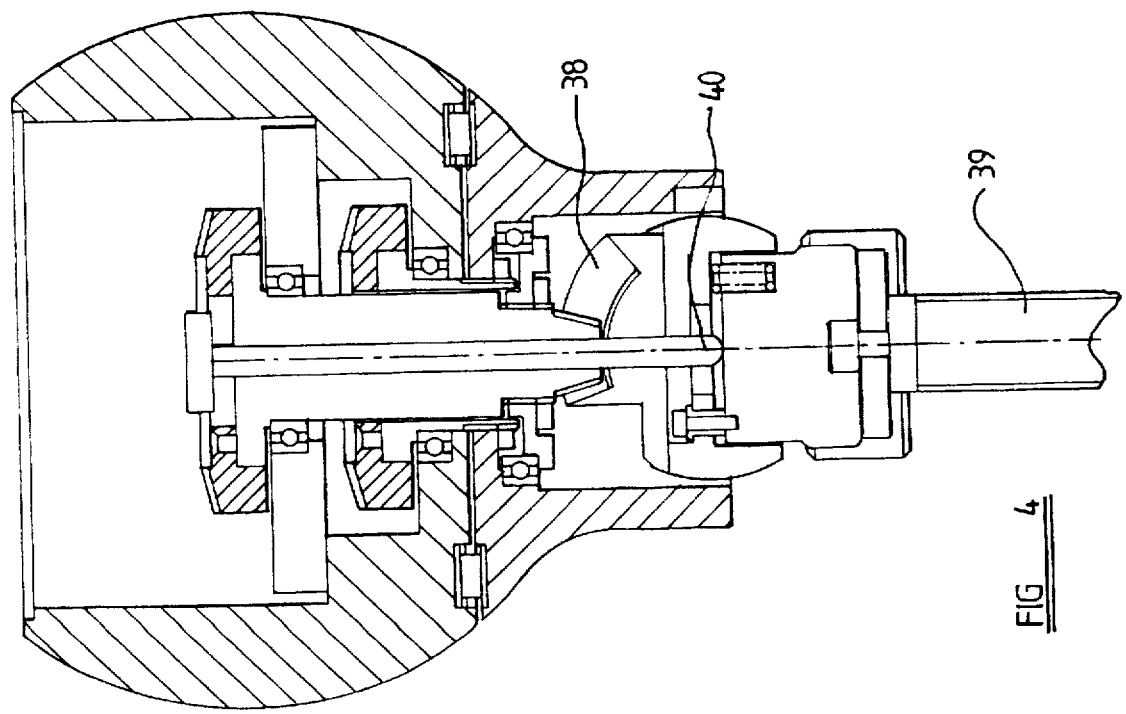
FIG. 4 is a further sectional view of the embodiment of FIG. 3.

Referring to FIGS. 3 to 5 of the drawings, a housing 30 is illustrated which can be utilised in the place of the motor housing 7 of the embodiment described above.

The housing 30 defines two inlet bores 31,32, each associated with bearings 33 so that each bore may contain a drive shaft. The drive shaft in the upper bore 31 is adapted to engage with a toothed pinion gear 34 which engages the periphery of a toothed crown wheel 35. The crown wheel 35 is adapted to drive a vertically located shaft 36, the shaft 36 terminating, at its lower end, with a pinion gear 37. The pinion gear 37 is adapted to co-operate with a part crown wheel 38. The part crown wheel 38 is effectively formed integrally with a shaft 39 that corresponds with the drive arm 8 of the embodiment described above. The shaft 39 is mounted for pivotal movement about a substantially horizontal axis 40. As can be seen in FIGS. 4 and 5, when the crown wheel 38 is caused to move relative to the pinion 37, the shaft 39 pivots about the pivot axis 40 from a vertical position to an inclined position.

The lower bore 32 is adapted to receive a drive shaft adapted to drive a toothed pinion gear 41 which engages the outer periphery of a toothed crown wheel 42. The toothed crown wheel 42 is of annular form and is located around the exterior of the shaft 36.

The crown wheel 42 drives a tubular drive member 43 which surrounds the shaft 36, the tubular member 43 firmly engaging a lower housing portion 44 and driving that lower housing portion 44 rotationally about a substantially vertical axis. The lower housing portion 44 supports the pivot 40 on which the shaft 39 is pivotally mounted.

It is thus to be appreciated that by driving the shaft in the upper bore 31, for example with a low torque motor, the shaft 39 may be moved, by means of the crown wheel-and-pinion arrangement, from a vertical position to an inclined position. By driving the shaft in the lower bore 32, for example with a low torque motor, the lower housing part 44 may be rotated about a vertical axis, thus causing the shaft 39 to be rotated about that axis.

Figure 6:
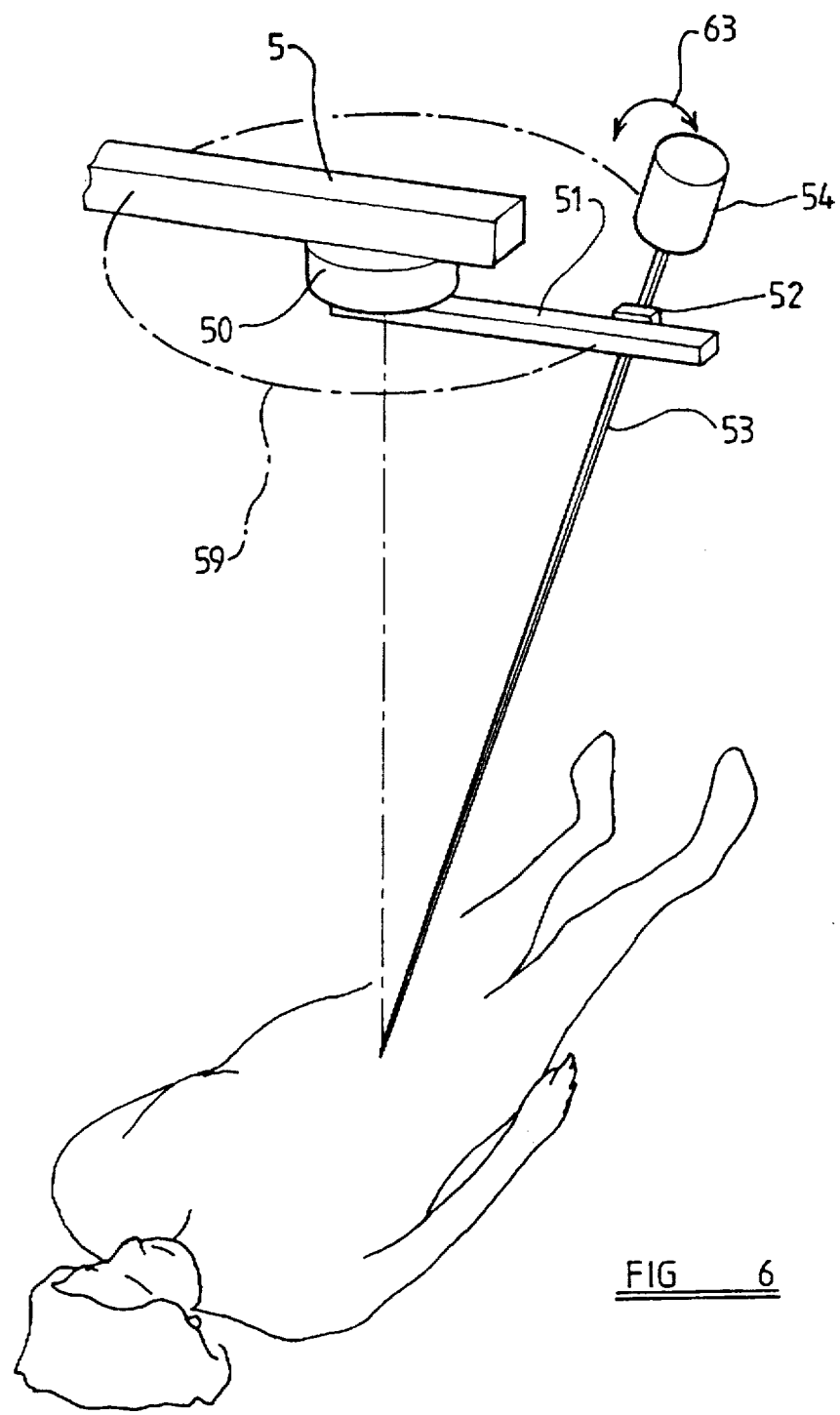
FIG. 6 is a schematic view of part of a further embodiment of the invention.

Referring now to FIG. 6 of the accompanying drawings, in a modified embodiment of the invention, the horizontal support beam 5 which will be associated with a housing, a vertical support column and a vertical support member of the type described with reference to FIG. 1, supports at its end a drive housing 50. Extending from the drive housing 50 is a horizontal arm 51. Carried on the horizontal arm 51 is a carriage 52 and, as will be described, means are provided for moving the carriage 52 axially along the arm 51. The carriage 52 is connected to a telescope 53, which is equivalent to the telescope 10 described above, and which is inserted into a patient as described above. The telescope 53 is provided with a camera 54 equivalent to the camera 11 described above.

Figure 7:
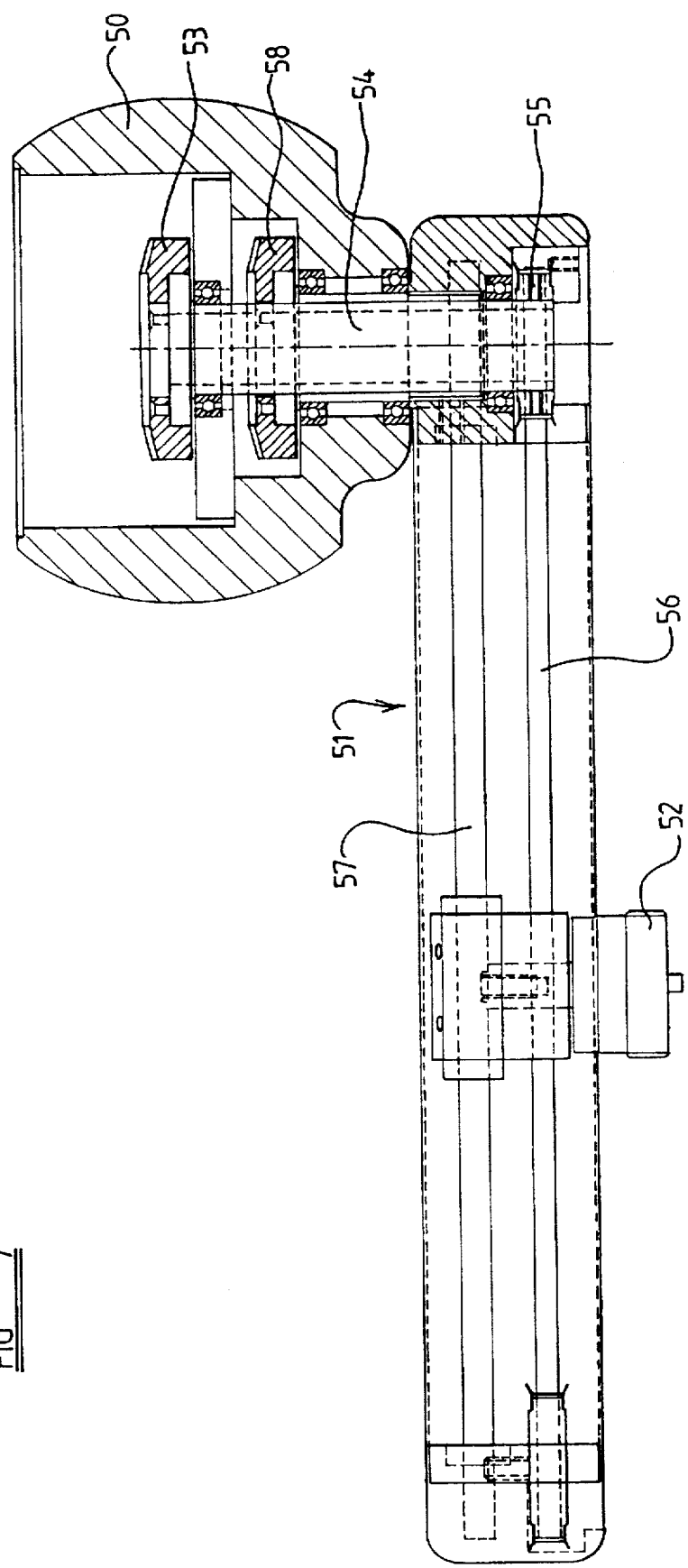
FIG. 7 is a sectional view of part of the embodiment of FIG. 6.

Referring now to FIG. 7, the drive housing 50 is illustrated in section, with the associated arm 51, showing the carriage 52. The drive housing 50 contains an upper crown wheel 53 which can be driven by an appropriate pinion gear. The crown wheel 53 drives a vertical shaft 54 which in turn drives a pulley 55 located within an end part of the arm 51. The pulley 55 drives a belt 56 which engages the carriage 52. The carriage 52 is supported for sliding movement along a rail 57 defined within the arm. Thus, by rotating the crown wheel 53 in the appropriate sense, the carriage 52 may be caused to move axially along the arm 51 with the carriage 52 moving along the rail 57.

A second crown wheel 58 located within the housing 50 may be driven by a second pinion. The crown wheel 58 is connected directly to the arm 51 and rotation of the crown wheel 58 causes the arm to rotate relative to the housing 50.

It is to be appreciated that the crown wheels 53 and 58 will be associated with pinion gears corresponding to the pinion gears 34 and 41 of the embodiment of FIG. 3, which are driven by low torque motors. Again, sufficiently low gearing may be utilised to permit backdriving.

It is to be understood, therefore, that the arm 51 may be caused to effect a rotational movement, causing the carriage to effect a horizontal circular movement as indicated by the circle 59 shown in FIG. 6. The carriage may be moved axially of the arm 51, thus altering the inclination of the cannula 53. Of course, if the carriage is moved axially of the arm 51, whilst the support beam 5 is raised or lowered, many different manoeuvres may be effected with the telescope. These manoeuvres will be goniometric.

It is to be appreciated that some laparoscopes have optically cranked lower ends. Thus, the field of view of the laparoscope is not axially aligned with the laparoscope, but is off-set to one side. It may, therefore, be desirable to rotate the laparoscope constituted by the telescope and the camera about its longitudinally axis in order to obtain a desired view of the interior of a patient. Consequently, the camera 11 may be provided with a motor adapted to rotate the entire camera and telescope as indicated schematically by the arrow 63 in FIG. 1.

The motor provided to rotate the camera 11 may be located in the camera housing or may preferably be located in the motor housing 7 being connected to the camera by a drive such as a Bowden cable.

What is claimed is:

1. A goniometric robotic arrangement, the arrangement comprising: an elongate telescope adapted to be inserted into the abdomen of a patient, a drive arm, the drive arm having a first part connected to means adapted to rotate the drive arm about a substantially vertical axis, the drive arm having a second part, spaced apart from the first part, which is rotated about said axis at a distance from the axis, connecting means comprising a loose articulation connecting said second part of the drive arm to the telescope, and drive means associated with the drive arm to adjust the angle of inclination of the drive arm and thus to adjust the angle of inclination of the telescope.

2. An arrangement according to claim 1 wherein the drive arm has an initial inclined position.

3. An arrangement according to claim 2 wherein the means adapted to adjust the angle of inclination of the drive arm comprise a crown wheel-and-pinion device.

4. An arrangement according to claim 3 wherein the crown wheel-and-pinion device is driven by a low torque motor.

5. An arrangement according to claim 1 wherein a carriage is provided which is movable along the drive arm, the carriage comprising said connecting means and being connected to the telescope, said drive means being adapted to move the carriage along the drive arm to effect the adjustment of the angle of inclination of the drive arm and thus to adjust the angle of inclination of the telescope.

6. An arrangement according to claim 5, wherein said means adapted to rotate the drive arm are supported by a horizontal support arm.

7. An arrangement according to claim 1 wherein the means adapted to rotate the drive arm are supported by support means, further drive means being provided to drive the support means in a vertical direction.

8. An arrangement according to claim 7 wherein the means adapted to drive the support means vertically comprise a hydraulic mechanism.

9. An arrangement according to claim 7 wherein the means adapted to drive the support means vertically comprise a recirculating ball drive.

10. A mechanism according to claim 9 wherein the recirculating ball drive is driven by a low torque motor.

11. An arrangement according to claim 7 wherein the support means comprises a substantially horizontally extending support beam, supported by an elongate substantially vertical support member, the said drive means being adapted to drive the support member.

12. An arrangement according to claim 11 wherein the support member is received within a housing, the housing being mounted on casters or the like.

13. An arrangement according to claim 1 wherein the means adapted to rotate the drive arm comprise a motor contained within a motor housing, a substantially vertical drive shaft driven by the motor being connected to one end of the drive arm.

14. An arrangement according to claim 1 wherein the telescope is associated with a camera provided at the upper end of the telescope.

15. An arrangement according to claim 14 wherein the lower end of the telescope is optically cranked.

16. An arrangement according to claim 15 wherein means are provided to rotate at least the lower end of the telescope relative to the axis of the telescope.

17. An arrangement according to claim 1 wherein the arrangement is provided with two light sources generating intersecting beams of light, the arrangement being such that the intersecting beams of light are adjusted to intersect at a position a predetermined distance beneath the upper end of the drive arm.

18. A goniometric robotic arrangement, the arrangement comprising:

an elongated telescope adapted to be inserted into the abdomen of a patient;

a drive arm connected to means adapted to rotate the drive arm about a substantially vertical axis;

connecting means connecting the drive arm to the telescope;

drive means associated with the drive arm to adjust the angle of inclination of the telescope; and a carriage moveable along the drive arm, the carriage comprising said connecting means and being connected to the telescope, said drive means being adapted to move the carriage along the drive arm to effect the adjustment of the angle of inclination of the drive arm and thus to adjust the angle of inclination of the telescope.

19. A goniometric robotic arrangement, the arrangement comprising:

an elongated telescope adapted to be inserted into the abdomen of a patient;

a drive arm connected to means adapted to rotate the drive arm about a substantially vertical axis;

connecting means connecting the drive arm to the telescope;

drive means associated with the drive arm to adjust the angle of inclination of the telescope; and two light sources generating intersecting beams of light, the arrangement being such that the intersecting beams of light are adjusted to intersect at a position a predetermined distance beneath the upper end of the drive arm.

* * * * *